United States Patent [19]

Khouri et al.

[11] Patent Number: 5,906,827
[45] Date of Patent: May 25, 1999

[54] MATRIX FOR THE MANUFACTURE OF AUTOGENOUS REPLACEMENT BODY PARTS

[75] Inventors: Roger K. Khouri, St. Louis, Mo.; Kuber T. Sampath, Medway; David C. Rueger, Hopkinton, both of Mass.

[73] Assignee: Creative BioMolecules, Inc., Hopkinton, Mass.

[21] Appl. No.: 08/253,398

[22] Filed: Jun. 3, 1994

[51] Int. Cl.[6] .............................. A61F 2/02; A61F 2/28; A61F 2/04; A61F 2/30

[52] U.S. Cl. ........................ 424/423; 424/491; 623/11; 623/12; 623/16; 623/18

[58] Field of Search .................. 623/11, 12, 16, 623/18; 424/423, 484, 491

[56] References Cited

U.S. PATENT DOCUMENTS

| | | |
|---|---|---|
| 4,385,404 | 5/1983 | Sully et al. . |
| 4,877,864 | 10/1989 | Wang et al. . |
| 4,880,429 | 11/1989 | Stone . |
| 4,968,590 | 11/1990 | Kuberasampath et al. . |
| 4,975,526 | 12/1990 | Kuberasampath et al. . |
| 5,011,691 | 4/1991 | Oppermann et al. . |
| 5,013,649 | 5/1991 | Wang et al. . |
| 5,041,138 | 8/1991 | Vacanti et al. . |
| 5,061,286 | 10/1991 | Lyle . |
| 5,067,940 | 11/1991 | Liboff et al. . |
| 5,067,962 | 11/1991 | Campbell et al. ................ 623/13 |
| 5,067,963 | 11/1991 | Khouri . |
| 5,067,964 | 11/1991 | Richmond et al. . |
| 5,108,753 | 4/1992 | Kuberasampath et al. . |
| 5,116,738 | 5/1992 | Wang et al. . |
| 5,154,189 | 10/1992 | Oberlander . |
| 5,171,574 | 12/1992 | Kuberasampath et al. . |
| 5,190,547 | 3/1993 | Barber, Jr. et al. ............... 606/79 |
| 5,206,023 | 4/1993 | Hunziker . |
| 5,258,494 | 11/1993 | Oppermann et al. . |
| 5,266,683 | 11/1993 | Oppermann et al. . |
| 5,270,300 | 12/1993 | Hunziker . |
| 5,326,357 | 7/1994 | Kandel . |
| 5,344,654 | 9/1994 | Rueger et al. . |
| 5,354,557 | 10/1994 | Oppermann et al. . |
| 5,413,989 | 5/1995 | Ogawa et al. . |
| 5,430,019 | 7/1995 | Rogers et al. ................... 514/12 |
| 5,492,697 | 2/1996 | Boyan et al. ................... 424/422 |
| 5,658,882 | 8/1997 | Celeste ........................... 514/12 |

FOREIGN PATENT DOCUMENTS

| | | |
|---|---|---|
| 0206801 | 6/1986 | European Pat. Off. . |
| 0567391A1 | 4/1993 | European Pat. Off. . |
| WO88/00205 | 1/1988 | WIPO . |
| WO89/09788 | 10/1989 | WIPO . |
| WO91/11366 | 10/1990 | WIPO . |
| WO 91/05802 | 5/1991 | WIPO . |
| WO91/18098 | 11/1991 | WIPO . |
| WO91/18558 | 12/1991 | WIPO . |
| WO93/00432 | 1/1993 | WIPO . |
| WO 93/25246 | 12/1993 | WIPO . |
| WO95/01131 | 6/1994 | WIPO . |
| WO94/26892 | 11/1994 | WIPO . |
| WO94/26893 | 11/1994 | WIPO . |
| WO95/16035 | 6/1995 | WIPO . |
| WO 96/36710 | 11/1996 | WIPO . |
| WO 96/39169 | 12/1996 | WIPO . |

OTHER PUBLICATIONS

Asch et al. ". . . Transplantation . . . of the Patella in the Rat", translation of Revue du Rheumatisme, 55(1), pp. 7–14, 1988.

Thomas et al., "An Improved Technique for Allogenic Hip Joint Implantations", Clinical Orthopaedics and Related Research, 106, pp. 86–93, Jan.–Feb. 1975.

Carr et al. "Clinical Evaluation of Freeze–Dried Bone Grafts", Journal of Bone and Joint Surgery, pp. 549–614 (1955).

Gresham, "The Freeze–dried Cortical Bone Homograft: A Roentgenographic and Histologic Evaluation", Clinical Orthopaedics and Related Research, 37, pp. 194–200 (1964).

Ham et al., "Histology", 6th ed., Lippincott Co., Phila, 1969 p. 397.

Johnson et al. "Repair of Segmental Defects of the Tibia with Cancellous Bone Grafts Augmented with Human Morphogenetic Protein", Clin. Orthop. 1988; 236: 249–257.

Johnson et al. "Resistant Nonunions and Partial or Complete Segmental Defects of Long Bones", Clin. Orthop. and Rel. Res. 1992; 277: 229–37.

Okada et al. "Experimental studies on half–joint transplantation", International Orthopaedics (1990) 14 261–7.

Prolo et al. "Ethylene Oxide Sterilization of Bone, Dura Mater, and Fascia Lata for Human Transplantation", Neurosurgery, vol. 6, No. 5, pp. 529–539 (May 1980).

Urist et al. "A Chemosterilized Antigen–Extracted Autodigested Alloimplant for Bone Banks", Archives of Surgery, vol. 110, pp. 416–428 (1975).

Urist "Surface–Decalcified Allogenic Bone (SDAB) Implants", Clin. Orthop. and Rel. Res. 1968; 56: 37–50.

Sampath et al. (1983), "Homology of Bone–Inductive Proteins From Human, Monkey, Bovine, and Rat Extracellular Matrix," Proc. Natl. Acad. Sci. USA 80:6591–6595.

Padgett et al. (1987), "A Transcript from a Drosophila Pattern Gene Predicts a Protein Homologous to the Transforming Growth Factor–B Family," Nature 325:81–84.

Sampath et al. (1987), "Dissociative Extraction and Reconstitution of Extracellular Matrix Components Involved in Local Bone Differentiation," Proc. Natl. Acad. Sci. USA 78:7599–7603.

Weeks (1987) "Maternal mRNA Localized to the Vegetal Hemisphere Xenopus Eggs Codes for a Growth Factor Related to TGF–β," Cell 51:861–867.

Wozney et al. (1988), "Novel Regulators of Bone Formation: Molecular Clones and Activities," Science 24:1528–1533.

(List continued on next page.)

Primary Examiner—Jeffrey C. Mullis
Attorney, Agent, or Firm—Testa, Hurwitz & Thibeault, LLP

[57] ABSTRACT

Disclosed are matrices, devices and methods for the manufacture of live autogenous skeletal replacement parts comprising plural different tissues.

9 Claims, 2 Drawing Sheets

OTHER PUBLICATIONS

Lyons et al. (1989), "VGR–1, A Mammalian Gene Related to Xenopus VG–1, is a member of the Transforming Growth Factor Beta Gene Superfamily," *Proc. Natl. Acad. Sci. USA* 4554–4558.

Celeste et al. (1990), "Identification of Transforming Growth Factor Beta Family Members Present in Bone–Inductive Protein Purified from Bovine Bone," *Proc. Natl. Acad. Sci. USA* 87:9843–9847.

Ozkaynak et al. (1990), "OP–1 cDNA Encodes an Osteogenic Protein in the TGF–$\beta$ Family," *Embo J.* 9:2085–2093.

Sampath et al. (1990), "Bovine Osteogenic Protein Is Composed of Dimers of OP–1 and BMP–2A, Two Members of the Transforming Growth Factor–B Superfamily," *J. Biol. Chem.* 265:13198–13205.

Wharton et al. (1991), "Drosophila 60A Gene, Another Transforming Growth Factor $\beta$ Family Member, is Closely Related to Human Bone Morphogenetic Proteins," *Proc. Natl. Acad. Sci. USA* 88:9214–9218.

Ozkaynak et al. (1992), "Osteogenic Protein–2," *J. Biol. Chem.* 267:25220–25227.

Prolo et al. "Ethylene Oxide Sterlization of Bone . . . ", Neurosurgery, vol. 6, No. 5, pp. 529–539 (May 1980).

Sampath et al. (1993), "Drosophila Transforming Growth Factor $\beta$ Superfamily Proteins Induce Endochondral Bone Formation in Mammals," *Proc. Natl. Acad. Sci. USA* 90:6004–6008.

Gresham, "The Freeze–dried Cortical Bone Homograft . . . ", Clinical Orthopaedics and Related Research, 37, pp. 194–200 (1964).

Urist et al. "A Chemosterilized . . . Alloimplant for Bone Banks" Archives of Surgery, vol. 110, No. 4, pp. 416–428 (1975).

Carr et al. "Clinical Evaluation of Freeze–Dried Bone Grafts", Journal of Bone and Joint Surgery, pp. 549–614 (1955).

Okada et al. "Experimental Studies on Half–joint Transplantation", International orthopaedics (1990) 14(3) 261–7.

Johnson et al. "Repair of Segmental Defects of the Tibia . . . ", Clin. Orthop. 1988; 236: 249–257.

Urist "Surface–Decalcified Allogenic Bone (SDAB) Implants", Clin. Orthop. 1968; 56: 37–50.

Johnson et al. "Resistant Nonunions and Partial or Complete Segmental Defects of Long Bones", Clin. Orthop. 1992; 277: 229–37.

FUNCTIONAL, VIABLE HEMIJOINT

=

MUSCLE FLAP SUPPLY OF STEM CELLS

+

OP-1 DIFFERENTIATION STIMULUS

+

LYOPHILIZED ALLOGRAFT STRENGTH, MATRIX AND SHAPE

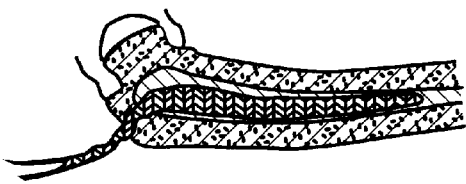
FIG. 2A CONTROL LYOPHILIZED ALLOGRAFT
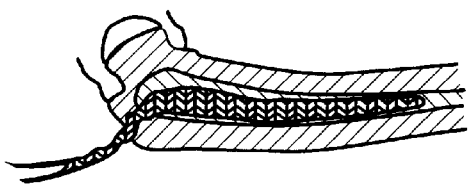
FIG. 2B ALLOGRAFT IMPREGNATED WITH OP-1
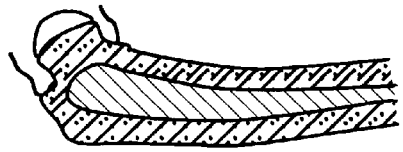
FIG. 2C ALLOGRAFT WITH MUSCLE FLAP IN MARROW CAVITY
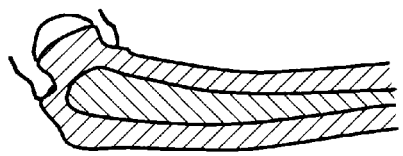
FIG. 2D ALLOGRAFT WITH OP-1 AND MUSCLE FLAP

MATRIX FOR THE MANUFACTURE OF AUTOGENOUS REPLACEMENT BODY PARTS

BACKGROUND OF THE INVENTION

This invention relates to a method of in situ manufacture of live autogenous replacement body parts such as skeletal parts, e.g. joints. More particularly, the invention is concerned with matrix materials and methods for the manufacture of live autogenous replacement parts comprising plural different tissues.

Bony defects, whether from degenerative, traumatic or cancerous etiologies, pose a formidable challenge to the reconstructive surgeon Although many types of bone grafts and numerous biocompatible materials have been used clinically they all suffer from shortcomings or potential long term complications See, for example, Urist, "Bone Transplants and Implants" in Fundamental and Clinical Bone Physiology, Chapter 11, Lippincott, Philadelphia, Pa., 1980 pp. 331–368; Habal and Reddi, "An Update on Bone Grafting and Bone Substitutes in Reconstructive Surgery" in Advances in Plastic and Reconstructive Surgery, Year Book Medical Publishers, Chicago, Ill., 1987, pp. 147–209.

More difficult still is the reconstruction or repair of skeletal parts comprising multiple different structural tissues. For example, joint reconstruction requires repair of both the bony defect and the articular cartilage. To date there are no satisfactory clinical means for readily repairing both cartilage and bony defects within a joint, and which result in viable, fully functional joints. Replacement with prosthetic joints is currently the only option for serious degeneration of joint function. It is anticipated that a means for functional reconstruction of joint complexes will have a profound effect on the management of degenerative joint disease and alloplastic joint replacement surgery.

True osteogenic factors capable of inducing the cascade of events that result in endochondral bone formation now have been identified, isolated and cloned. These proteins, when implanted in a mammal, typically in association with a matrix that allows the attachment, proliferation and differentiation of migratory progenitor cells, are capable of inducing recruitment of progenitor cells, stimulating their proliferation and inducing differentiation into chondrocytes and osteoblasts, and inducing differentiation of cartilage, vascular invasion, bone formation, remodeling, and finally marrow differention. More recently, these factors have been shown capable of generation of tissue of mesenchynal origin more generally, including liver and nerve tissue.

A particularly useful osteogenic protein is human OP1 (Osteogenic Protein-1), described in U.S. Pat. No. 5,011,691, U.S. Pat. No. 5,266,683 the disclosures of which are incorporated by reference and Ozkaynak et al. (1990) *EMBO J.* 9: 2085–2093. Species homologs identified to date include mouse OP-1 (see U.S. Pat. No. 5,266,683) and the Xenopus homolog 60A, described in Wharton et al. (1991) *PNAS* 88:9214–9218). Other closely related proteins include OP2 (Ozkaynak (1992) *J. Biol. Chem.* 267:25220–25227 and U.S. Pat. No. 5,266,683), BMP5, and 6 (Celeste et al. (1991) *PNAS* 87:9843–9847) and Vgr-1 (Lyons et al. (1989). These disclosures disclose the sequences and chemical and physical characteristics of these proteins. U.S. Pat. Nos. 5,011,691 and 5,266,683 also provide detailed descriptions for formulating and assaying osteoinductive devices useful for inducing bone formation in mammals. Other related osteoinductive proteins include BMP 2, 3, 4 (Wozney et al. (1988) *Science* 242:1528–1534); BMP 9 (WO93/00432, published Jan. 7, 1993); DPP (Padgett et al. (1987) *Nature* 325:81–84, and Vg-1 (Weeks (1987, *Cell* 51:861–867).

It is an object of the instant invention to provide a matrix suitable for regenerating body parts comprising two or more functionally and structurally associated different replacement tissues in an animal. It is another object to provide devices and methods for the reconstruction of viable, functional body parts comprising plural tissues, e.g., organs such as liver or joints comprising new bone and articular/cartilage.

SUMMARY OF THE INVENTION

In accordance with the present invention a novel matrix is provided for the manufacture of a live autogenous replacement part comprising plural distinct tissues.

More particularly, on one aspect, the invention provides a matrix for forming a functional, mammalian, replacement body part comprising plural distinct tissues. The matrix comprises the intact, typically but not necessarily metabolically inert, i.e., dead, residue of an allogenic or xenogenic body part, excised from a mammalian donor, such as a cadaver. The body part may be dehydrated such as by lyophilization so that no residual cellular metabolism remains, but the function of endogenous growth factors and the like can be restored upon in situ reconstitution by endogenous body fluids. The treated body part which becomes the matrix includes the residues of the plural distinct tissues constituting the body part sought to be replaced. Furthermore, the residues constituting the matrix have dimensions and a structural relationship to each other which mimic that of the body part to be replaced. Disposed on the surfaces of the residues is an osteogenic or morphogenic protein present in an amount sufficient to induce formation of each of the plural tissues in place. This permits regeneration of the body part within the mammal including plural tissues of appropriate size, interrelationship, and function.

The matrix preferably is made from, and designed to replace, at least a portion of a skeletal joint, and comprises at least cartilage and bone.

The matrix also may comprise an "osteogenic devices", i.e., a particulate, resorbable carrier associated with osteogenic protein. The device is disposed within a hollow portion of the allogenic or xenogenic body part, e.g., within the marrow cavity of the residue of a portion of a bone. The nature of such devices is disclosed in detail in the patents referenced above.

In another aspect, the invention provides a method of replacing a defective body part. The method comprises the steps of surgically excising the defective body part, implanting a matrix of the type described above at the site of excision, and, if necessary, surgically repairing tissues adjacent the site of excision. For example for joint replacement, it is often necessary to repair the bursa and other structure in the vicinity of the joint, so as to maintain an environment at the implant site as close to normal as possible. It also often is necessary to suture or otherwise mechanically temporarily connect the implanted matrix to surrounding tissue. It is preferred but not required to include in the practice of the method the additional steps of implanting a muscle flap into a hollow portion of the allogenic or xenogenic body part.

In one embodiment, the matrix comprises a physiologically inert support material suitable for inducing tissue morphogenesis of both bone and articular cartilage. The matrix also preferably is biocompatible and biodegradable in vivo. The matrix comprises an allograft of the joint to be replaced, comprising both the bone and associated articular cartilage, which tissues optionally may be treated, e.g., prior to implantation, to destroy the metabolic viability of the structures. Currently preferred is a lyophilized or otherwise dehydrated or alcohol extracted allograft. A detailed description of suitable chemical treatment of such matrices is described in U.S. Ser. No. 07/091,395, filed Jul. 13, 1993, the disclosure of which is incorporated herein by reference. After application of osteogenic protein to its surface, the matrix can be used to generate a functional, autograft replacement by implanting the coated allograft at the defective skeletal site and allowing time for tissue morphogenesis to occur.

Regeneration of the necessary tissues, e.g., bone, bone marrow and articular cartilage in the case of a replacement joint, occurs during resorption in place of the implanted allograft, i.e., replacing the implanted matrix in shape, size, and proper location while maintaining interrelationships of tissues. In one embodiment, using the method of Khouri, U.S. Pat. No. 5,067,963, the disclosure of which is incorporated herein by reference, a muscle flap, which may or may not itself be pretreated with osteogenic protein, can be surgically introduced into a cavity in the implanted matrix to provide a blood supply to support faster tissue morphogenesis and a ready supply of mesenchymal stem cells necessary to initiate the cascade of replacement by new tissue formation.

The osteogenic protein can be, for example, any of the known bone morphogenetic proteins described hereinabove and/or in the art and includes naturally sourced material, recombinant material, and any material otherwise produced which is capable of inducing tissue morphogenesis. See U.S. Ser. No. 07/752,764, filed Mar. 30, 1991, now abandoned the disclosure of which is incorporated herein by reference. Preferably, the protein is OP1 or a related protein.

The matrix of the invention and/or the tissues which result from its use, essentially satisfy the following criteria of a preferred grafting material:

1. It is autogenous. Because it originates from the patient the graft does not become subject to immune rejection.
2. It results in formation of the plural necessary, live vascularized functional tissues normally present at the site, of an appropriate size, and having correct structural relationships so as to result in a functional body part. Live vascularized bone and/or cartilage autografts or other autografts can be formed at one location in the body of a patient and then transplanted to their position and orientation of use, i.e., surgically implanted so as to preserve an intact microcirculation, blood perfusion, and other interconnection to circulatory system parts as required at the recipient site. These transplanted, in-situ generated autografts heal in a fashion similar to that of simple fractures. Most importantly, whether produced in situ at the site of intended use or remotely, the multi-tissue replacement part so produced becomes incorporated, integrating with adjacent tissues, essentially maintaining its shape, and avoiding abnormal resorption, regardless of the conditions present at the recipient site [Weiland et al., Clin. Orthop. 174, 87 (1983)].
3. It is capable of being precisely contoured and shaped to exactly match any defect, whichever complex skeletal or organ shape it is meant to replace.
4. It has virtually unlimited supply and is relatively easy to obtain.
5. It has minimal donor site morbidity.

BRIEF DESCRIPTION OF THE DRAWINGS

While the specification concludes with claims particularly pointing out and specifically claiming the subject matter which is regarded as constituting the present invention, it is believed that the invention will be better understood from the following detailed description of preferred embodiments taken in conjunction with the accompanying drawings in which:

FIGS. 2A through 2D are schematic representations of the four allografts tested in the hemijoint example.

DETAILED DESCRIPTION

In order to illustrate the invention in greater detail, the following illustrative reconstructive surgery was carried out, wherein a functional, viable joint was reconstructed from a resected gleno-humeral hemiarticular complex. It will be appreciated that the invention is not limited to this exemplary work or the specific details set forth in these examples.

Reconstruction of a Hemi-Joint

New Zealand White rabbits were used as the experimental model, and 10 rabbits each were used for the four groups described below. The same number of rabbits served as donors and recipients. Standard orthopedic surgical equipment and procedures were used.

In the rabbits, joint defects were created by surgically resecting the entire gleno-humeral hemiarticular complex with the proximal ⅔ of the humerus. Allografts for implantation were prepared from hemijoints with the articular surface of the glenohumoral joint. All allografts were lyophilized using standard procedures to destroy viability of the material. Follow-up evaluations were obtained by serial weekly radiographs (X-rays and magnetic resonance imaging), and with histology and mechanical testing at sacrifice 5 weeks after the surgery.

All lyophilized, osteogenic protein-treated allografts were coated with OP1 as described in U.S. Pat. No. 5,011,691. Briefly, matures dimeric recombinant OP-1 was solubilized in an acetonitrile trifluoro-acetic acid solution, combined with the allograft matrix, and lyophilized. A single donor provided both humeral heads to the same recipient with an OP-1 treated side and a contralateral control. The allograft matrices were secured in place with a four hole titanium miniplate. A meticulous surgical reconstruction of the joint capsule was performed to atraumatically restore the synovial milieu of the grafted articular surface. Motion was permitted almost immediately after surgery, again to restore normal joint conditions.

Figure 1:
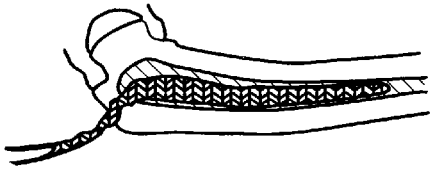
FIGS. 1A through 1D are schematic representation of the elements used to generate a viable, functional hemijoint in one embodiment of the invention.
Figure 1:
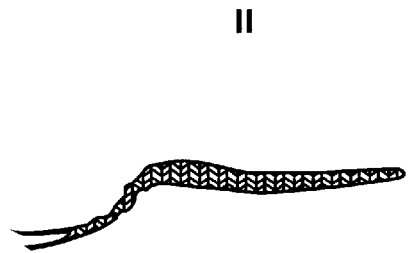
Figure 1:
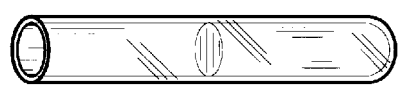
Figure 1:
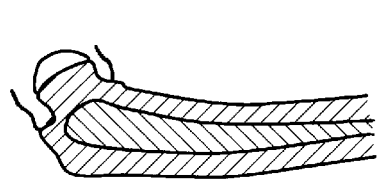

In some animals, local muscle flaps (cutaneous maximus muscle) were incorporated into the region of the defect, threaded into the marrow cavity of the allograft using the method of Khouri. (see FIGS. 1,2).

Four groups of implanted lyophilized allografts thus were studied. See FIGS. 2A, 2B, 2C, and 2D. In Group 1, control, lyophilized allografts, free of osteogenic protein, were implanted (FIG. 2A). In Group 2, the lyophilized allografts were impregnated with OP1 prior to implantation (FIG. 2B). In Group 3, controls lyophilized allografts, free of osteogenic protein, were implanted with muscle flap threaded into the marrow cavity (FIG. 2C). In Group 4, lyophilized allografts were pretreated with OP1 as described above and in more detail in U.S. Pat. No. 5,011,691, and muscle flaps were implanted (FIG. 2D).

In all cases graft healing was followed noninvasively with serial x-rays and standard MRI (magnetic resonance imaging). on plain x-rays, all allografts treated with OP1 produced a noticeably thickened cortex by 1 week, as compared with control allografts (Groups 1, 3) which evidenced only a thin egg-shell-like cortex. By four weeks all control allografts had fractured and were unstable. In contrast, OP-1 treated allografts (Groups 2, 4) remained stable.

MRI was used as a noninvasive means for following reformation of articular cartilage in the allografts. A dark signal produced by MRI represents absent or nonviable cartilage, while a bright signal indicates live, viable cartilage. All control allografts produced only a dark signal, when tested at 1, 3 and 5 weeks. These MRI findings were confirmed by histological analysis performed at 5 weeks. Sagital sectioning through control allografts showed a degenerated articular surface with no live cells.

By contrast, the MRI findings of the articular caps on OP1-treated allografts showed a bright signal by week 3, indicating the regeneration of viable cartilage. Histological analysis of the OP1-treated allografts at week 5 revealed a layer of newly generated articular cartilage on top of the allograft matrix. The allografts of Group 4 showed somewhat thicker cartilage layers than those of Group 2, suggesting that the addition of the muscle flap may enhance the rate of joint regeneration.

Finally, joints regenerated with the OP-1 treated allografts regained normal range of motion by the time they were harvested at 5 weeks post-reconstruction. By contrast, the harvested control allografts were stiff and contracted at the 5 week time of harvest.

What is claimed is:

1. A matrix for forming a stable functional, replacement skeletal joint comprising articular cartilage and bone tissues at a skeletal joint defect site in a mammal, the matrix comprising:

a biocompatible, bioresorbable, devitalized support material, excised from a mammalian donor skeletal joint and, including devitalized bone and associated articular cartilage tissues capable of essentially maintaining their shape and interrelationships of tissues when used as a replacement joint, said devitalized tissues having dimensions and structural relationships to each other which correspond anatomically to those of the skeletal joint to be replaced, and, disposed on the surfaces of said matrix, substantially pure exogenous osteogenic protein in an amount sufficient to induce formation of new said bone and associated articular cartilage tissues thereby to permit regeneration of said functional, replacement skeletal joint at said defect site within said mammal.

2. The matrix of claim 1 wherein said bone and articular cartilage tissues are devitalized by dehydration.

3. The matrix of claim 1 further comprising a particulate, resorbable carrier associated with exogenous osteogenic protein, disposed within a hollow portion of said matrix.

4. A method of replacing a defective skeletal joint comprising the steps of surgically:

(a) excising said defective skeletal joint; and (b) implanting the matrix of claim 1, 2 or 3 at the site of excision.

5. The method of claim 4 comprising the additional steps of implanting a muscle flap into a hollow portion of said matrix.

6. The matrix of claim 1 wherein said exogenous osteogenic protein is selected from the group consisting of: OP-1, OP-2, BMP5, BMP6, BMP2, BMP3, BMP4, BMP9, DPP, Vg-1, 60A, Vgr-1, including naturally sourced and recombinant derivatives of the foregoing.

7. The matrix of claim 1 wherein said exogenous osteogenic protein is selected from the group consisting of: OP-1, OP-2, BMP2, BMP3, BMP4, BMP5, BMP6, including naturally sourced and recombinant derivatives of the foregoing.

8. The matrix of claim 1 wherein said exogenous osteogenic protein is OP-1 or a related osteogenic protein.

9. The matrix of claim 1 wherein said exogenous osteogenic protein is OP-1.

* * * * *